US008601869B2

(12) United States Patent
Miller (10) Patent No.: US 8,601,869 B2
(45) Date of Patent: Dec. 10, 2013

(54) MULTI-FUNCTIONAL HAND STRENGTH ASSESSMENT DEVICE

(76) Inventor: Mark Carl Miller, Oakmont, PA (US)

( * ) Notice: Subject to any disclaimer, the term of this patent is extended or adjusted under 35 U.S.C. 154(b) by 189 days.

(21) Appl. No.: 13/306,441

(22) Filed: Nov. 29, 2011

(65) Prior Publication Data
US 2012/0137772 A1 Jun. 7, 2012

Related U.S. Application Data (60) Provisional application No. 61/417,671, filed on Nov. 29, 2010.

(51) Int. Cl.
*A61B 1/24* (2006.01)

(52) U.S. Cl.
USPC ....................................................... 73/379.02

(58) Field of Classification Search
USPC .............................. 73/379.01, 379.02, 379.03
See application file for complete search history.

(56) References Cited

U.S. PATENT DOCUMENTS

| | | | |
|---|---|---|---|
| 2,708,367 A | 5/1955 | Lusk | |
| 3,542,363 A | 11/1970 | Bishop | |
| 3,672,219 A | 6/1972 | Van Patten | |
| 4,674,330 A | 6/1987 | Ellis | |
| 4,884,445 A | 12/1989 | Sadoff et al. | |
| 4,949,729 A * | 8/1990 | Haski | 600/587 |
| 5,125,270 A | 6/1992 | Kovacevic | |
| 5,157,970 A | 10/1992 | Lewis, Jr. | |
| 5,170,663 A | 12/1992 | Kovacevic | |
| 1,903,352 A | 4/1993 | Ramsey | |
| 5,299,457 A | 4/1994 | Pang et al. | |
| 5,317,916 A | 6/1994 | Kovacevic | |
| 5,398,696 A * | 3/1995 | Wiley | 600/587 |
| RE35,598 E | 9/1997 | Sadoff et al. | |
| 6,186,961 B1 * | 2/2001 | Hanoun | 600/587 |
| 6,868,710 B2 | 3/2005 | Becker et al. | |
| 7,127,944 B1 | 10/2006 | Rozmaryn | |
| 7,152,471 B2 | 12/2006 | Baratz et al. | |
| 7,448,265 B2 * | 11/2008 | Smyser et al. | 73/379.02 |
| 7,467,551 B1 | 12/2008 | Yang | |
| 7,470,217 B2 | 12/2008 | Jones-Glaser | |
| 7,975,543 B2 * | 7/2011 | Clem et al. | 73/379.02 |

* cited by examiner

*Primary Examiner* — Jewel V Thompson
(74) *Attorney, Agent, or Firm* — The Webb Law Firm, P.C.

(57) ABSTRACT

A multi-functional hand strength assessment device includes a housing and at least one bellows device supported by the housing. A grip bar is interfaced with the bellows device for compression thereof. The grip bar is supported by the housing and is accessible by a user to grasp the grip bar for assessment of grip hand strength and finger pinch strength of the user. A grip is interfaced with the bellows device for compression thereof for assessment of twisting hand strength of the user. A pinch bar is supported by the housing opposite the grip bar and movement of one of the grip bar and the pinch bar towards the other compresses the bellows device for assessment of finger pinch strength of the user's fingers. A mechanical or electronic pressure gauge is in fluid connection with the bellows device to register a reading relating to hand strength.

26 Claims, 8 Drawing Sheets

MULTI-FUNCTIONAL HAND STRENGTH ASSESSMENT DEVICE

RELATED APPLICATION

This application claims the benefit of U.S. Provisional Patent Application No. 61/417,671 filed Nov. 29, 2010 entitled "Multi-Functional Hand Strength Assessment Device", which is incorporated herein in its entirety by reference.

BACKGROUND OF THE INVENTION

1. Field of the Invention

The multi-functional hand strength assessment device permits quantification of three aspects of hand strength: grip hand strength, finger pinch strength, and twisting hand strength.

2. Description of Related Art

This disclosure is directed to the field of medical apparatus used to measure the grip strength of a person's hand, the pinch strength between two digits of the hand, and twisting or torque strength of a person's hand. It is useful for doctors to be able to objectively monitor the progress of patients who have suffered hand injury, either through accidents or debilitating diseases, such as arthritis, or who have undergone hand surgery.

Numerous devices are known in the medical field for measuring aspects of human hand strength. U.S. Pat. No. 2,708,367 to Lusk discloses a force dynamometer adapted to measure hand strength. The Lusk hand grip measurement device utilizes a force gauge that measures the applied force remotely from the point of application by means of hydraulic pressure transmitted through a liquid filled connection of pre-set length. U.S. Pat. No. 3,672,219 to Van Patten discloses a handgrip dynamometer equipped with an electric transducer which is connected to a volt meter. U.S. Pat. No. 4,674,330 to Ellis discloses an apparatus for measurement of both the grip strength of a person's hand and pinch strength of two digits of the hand. The Ellis apparatus comprises two parallel grip handles extending at right angles from a third member. A handle is rigidly fixed to the third member and has two pairs of strain gauges mounted thereon to measure the force applied to the handles irrespective of where that force is applied. The grip handles are adjustable with respect to the strain gauge handle to alter the distance between the grip handles which terminate in flat portions to be used for measurement of pinch strength.

A traditional device used to assess grip strength in the clinical setting as well as in experimental investigation is the Jamar® dynamometer. U.S. Pat. No. 4,884,445 to Sadoff et al. discloses an otherwise conventional Jamar® dynamometer that is provided with a force transducer. The analog output of the force transducer is sampled at regular intervals and converted to a sequence of digital values by a conventional analog-to-digital converter. The digital output of the converter is processed by a conventional computer in real time to produce an output that clearly indicates the maximum force exerted by the test subject. The output may be both a graphic display of the forces exerted by the test subject over a predetermined interval of time and a statistical analysis of those forces.

U.S. Pat. No. 4,949,729 to Hash discloses a hand grip assessment apparatus that comprises a fluid filled compressible object, such as an inflatable bladder, and a pressure transducer in fluid communication with the inflatable bladder. The pressure transducer is connected to a circuit used to determine the rate of change with time of the logarithm of the pressure of the fluid in the inflatable bladder between predetermined lower and upper pressure levels. This information is displayed and/or recorded for hand grip assessment purposes.

U.S. Pat. No. 5,125,270 to Kovacevic discloses a human hand load sensor that uses a strain gauge force measurement instrument which has two platforms or handles that can be moved together with parts of the human hand, for example, a thumb and finger, or the handles can be grasped between the heel of the hand and several fingers. The instrument permits measuring of strength force by supporting a movable handle relative to a base or reference handle through a flexure system which deforms predictably under shear loading as the handles or platforms are moved together.

U.S. Pat. No. 5,157,970 to Lewis, Jr. discloses a hand grasp analysis apparatus and method by which the power of grasp exerted by the human hand can be measured. The apparatus includes a housing having opposed walls which can be forced towards one another in proportion to the magnitude of the compressive strength exerted by the person that grasps the housing. A transducer enclosed within the housing is compressed between the movable opposed walls and provides a signal that is proportional to the magnitude of the compressive force of the grasp. The signal is converted into a measurement indicative of the magnitude of the force.

U.S. Pat. No. 5,170,663 to Kovacevic discloses a grip sensor that is formed from a unitary block having upper and lower covers. The grip sensor comprises two sets of parallel flexure beams connected between outer end blocks and a center block and are loaded by a base plate connected to the outer end block and extending between the end blocks. The flexure beams deflect to respond to hand grip strength. Strain sensors located on the flexure beams and connected in a wheatstone bridge provide indication of gripping strength.

U.S. Pat. No. 5,299,457 to Pang et al. discloses a grip meter that includes a frame, a base on the frame sized and shaped to engage the palm of the hand, a plurality of plungers on the frame opposite the base and located for being depressed by corresponding fingers of the hand, and a device associated with the base and the plungers for simultaneously measuring and recording both finger strength and overall hand strength. The disclosed grip meter is symmetrical so that it can be used for measuring the finger and hand strength of either the left hand or the right hand.

U.S. Pat. No. 5,317,916 to Kovacevic discloses a digit grip sensor for measuring the grip strength of the human hand. The digit grip sensor comprises a post support having a first and a second sensor therein. A first post extends through the first sensor and a second post extends through the second sensor. A crossbar spaced from the post support extends between the first post and the second post. Each sensor has a plurality of strain gauges mounted thereon for measuring the deflection of the sensor. The crossbar can have a plurality of individual digit sensors mounted thereon for measuring the contributions of each finger to the grip force. The crossbar and the individual digit sensors can be adjusted for various hand and finger sizes.

U.S. Pat. No. 7,152,471 to Baratz et al. lists as an inventor the inventor of the subject disclosure. This patent discloses an apparatus and method for determining the strength of the hand based on a twisting action with the hand.

U.S. Pat. No. 7,467,551 to Yang discloses a grip strength detection device which includes a handle for the user to hold and apply a force, the movement of which drives a cable which rotates a shaft. A disk is connected to an end of the shaft and includes protrusions which pass through a photoelectric sensor so as to detect the angular distance that the disk travels. The angular distance is transferred into the value of the grip strength.

U.S. Pat. No. 7,470,217 to Jones-Glaser discloses a grip strength device that is configured to gauge the grip strength of contracted muscles or aid in exercising particular muscles by providing resistance against the contracted muscles. The grip strength device has a removable casing containing a first fluid, a first bellows, a second bellows, and a pressure gauge. The first bellows has a closed end and a first valve in communication with the casing. The second bellows has a second fluid. The second bellows has a second valve connected to the pressure gauge and a closed end abutting the closed end of the first bellows. Pressure applied to the removable casing is communicated from the first bellows to the second bellows and measured by the pressure gauge.

SUMMARY OF THE INVENTION

While the foregoing illustrates numerous hand grip assessment devices, none of the foregoing devices is multi-functional. The multi-functional hand strength assessment device described in detail herein permits quantification of three aspects of hand strength: grip hand strength, finger pinch strength, and twisting hand strength.

A multi-functional hand strength assessment device according to one embodiment comprises a housing, at least one bellows device supported by the housing, a grip bar interfaced with the bellows device for compression thereof, and a grip interfaced with the bellows device for compression thereof. The grip bar is supported by the housing to be accessible by a user to grasp the grip bar for selective assessment of grip hand strength and finger pinch strength of the user. The grip is interfaced with the bellows device for compression thereof for assessment of twisting hand strength of the user.

The multi-functional hand strength assessment device may further comprise a pinch bar supported by the housing opposite the grip bar and movement of one of the grip bar and the pinch bar towards the other compresses the bellows device for assessment of finger pinch strength of the user's fingers. The grip bar may comprise an upstanding pinch tab for contact by the user's fingers. A pressure gauge may be in fluid connection with the bellows device, such as a mechanical pressure gauge or an electronic pressure gauge. At least one suction cup may be provided on the bottom of the housing for securing the housing to a support surface.

The grip bar may be in contact engagement with the bellows device such that linear movement of the grip bar compresses the bellows device. The grip may be interfaced with the bellows device via a pivotal beam connected to the grip such that rotational movement of the grip pivots the beam and compresses the bellows device.

In another embodiment, the multi-functional hand strength assessment device comprises a housing, at least one bellows device supported by the housing, a grip bar interfaced with the bellows device for compression thereof, and a pinch bar supported by the housing opposite the grip bar. The grip bar is supported by the housing to be accessible by a user to grasp the grip bar for assessment of grip hand strength. In use, movement of one of the grip bar and the pinch bar towards the other compresses the bellows device for assessment of finger pinch strength of the user's fingers. The grip bar may comprise an upstanding pinch tab for contacting by the user's fingers. A pressure gauge may be in fluid connection with the bellows device, such as a mechanical pressure gauge or an electronic pressure gauge. At least one suction cup may be provided on the bottom of the housing for securing the housing to a support surface.

In a further embodiment, the multi-functional hand strength assessment device comprises a housing, at least one bellows device supported by the housing, a grip bar interfaced with the bellows device for compression thereof, and a grip interfaced with the bellows device for compression thereof. The grip bar is supported by the housing to be accessible by a user to grasp the grip bar for assessment of grip hand strength. The grip is interfaced with the bellows device for compression thereof for assessment of twisting hand strength of the user. A pressure gauge may be in fluid connection with the bellows device, such as a mechanical pressure gauge or an electronic pressure gauge. At least one suction cup may be provided on the bottom of the housing for securing the housing to a support surface.

The grip bar may be in contact engagement with the bellows device such that linear movement of the grip bar compresses the bellows device. The grip may be interfaced with the bellows device via a pivotal beam connected to the grip such that rotational movement of the grip pivots the beam and compresses the bellows device.

Another aspect of this disclosure relates to a method of operating a multi-functional hand strength assessment device. A step in the method provides the multi-functional hand strength assessment device, which comprises a housing, at least one bellows device supported by the housing, a grip bar interfaced with the bellows device for compression thereof, and a grip interfaced with the bellows device for compression thereof. Thereafter, a user may grasp the grip bar or the grip and actuate the selected grip bar or grip to compress the bellows device.

At least one suction cup may be provided on the bottom of the housing, and the method may comprise securing the housing to a support surface using the at least one suction cup.

The grip bar is desirably in contact engagement with the bellows device, and the method may further comprise effecting linear movement of the grip bar to compress the bellows device. Additionally, the grip is desirably interfaced with the bellows device via a pivotal beam connected to the grip, and the method may further comprise effecting rotational movement of the grip to pivot the beam and compress the bellows device.

A pinch bar may be supported by the housing opposite the grip bar, and the method may further comprise moving one of the grip bar and the pinch bar towards the other to compress the bellows device.

A pressure gauge may be in fluid connection with the bellows device, and the method may further comprise assessing grip hand strength, finger pinch strength, or twisting hand strength of the user using the pressure gauge upon compression of the bellows device.

Further details and advantages will become clear from the following detailed description read in conjunction with the accompanying drawings, wherein like numerals represent like parts throughout.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, and features illustrated in the accompanying drawing figures and described herein are simply exemplary and should not be considered as limiting.

Figure 1:
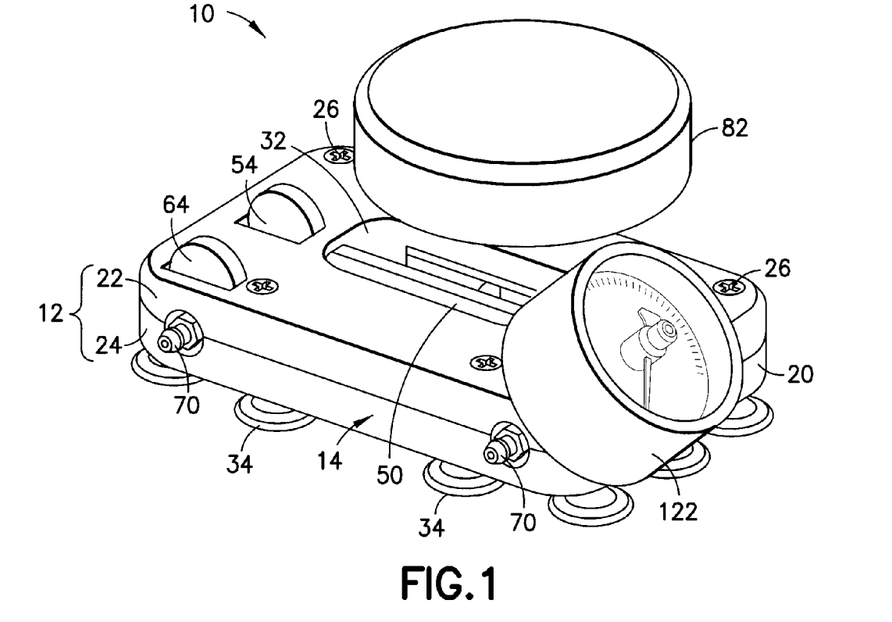
FIG. 1 is a front perspective view of a multi-functional hand strength assessment device.
Figure 2:
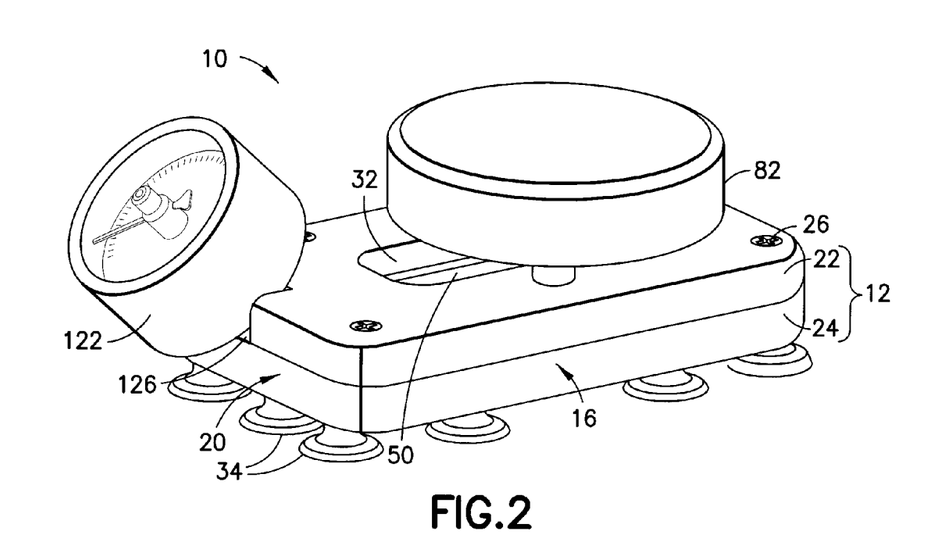
FIG. 2 is a rear perspective view of the multi-functional hand strength assessment device shown in FIG. 1.
Figure 3:
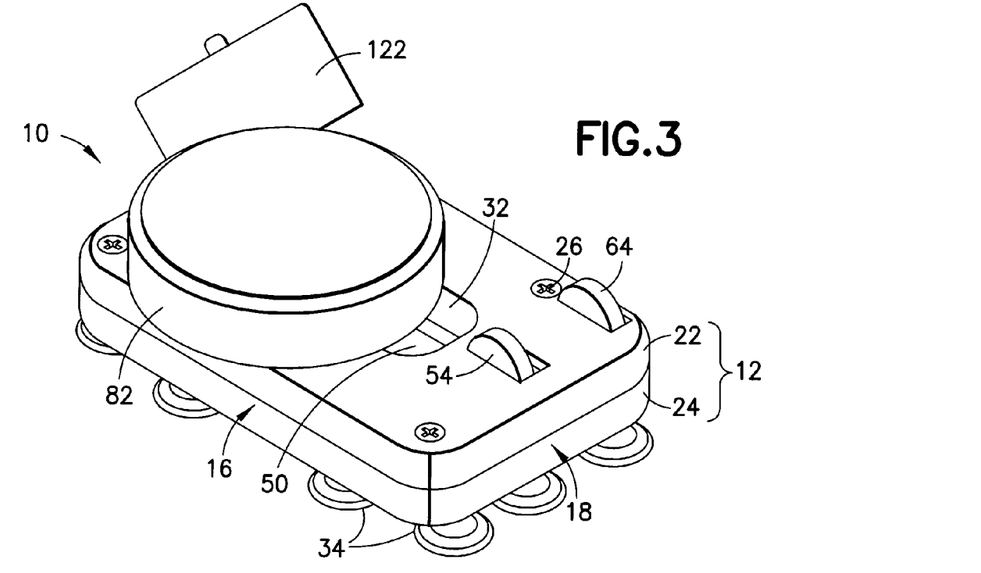
FIG. 3 is generally a top perspective view of the multi-functional hand strength assessment device shown in FIG. 1.
Figure 4:
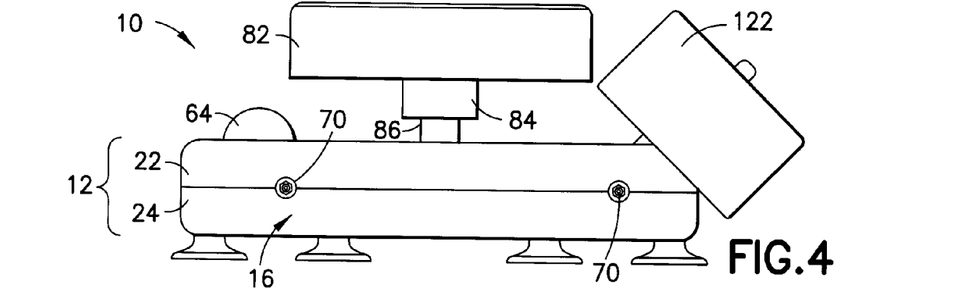
FIG. 4 is a front view of the multi-functional hand strength assessment device shown in FIG. 1.
Figure 5:
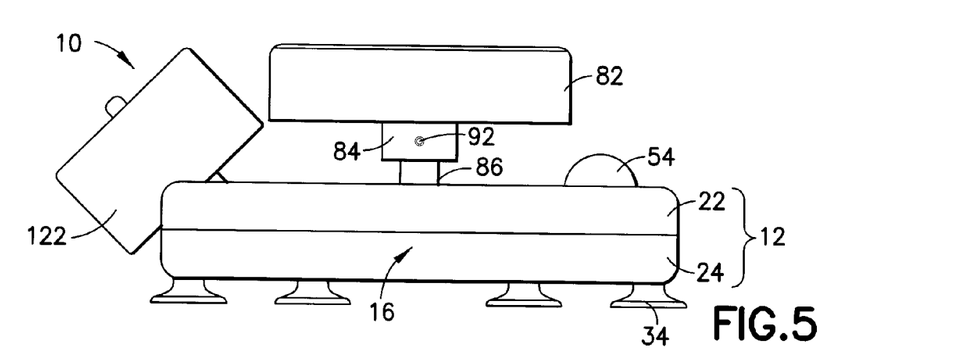
FIG. 5 is a rear view of the multi-functional hand strength assessment device shown in FIG. 1.
Figure 6:
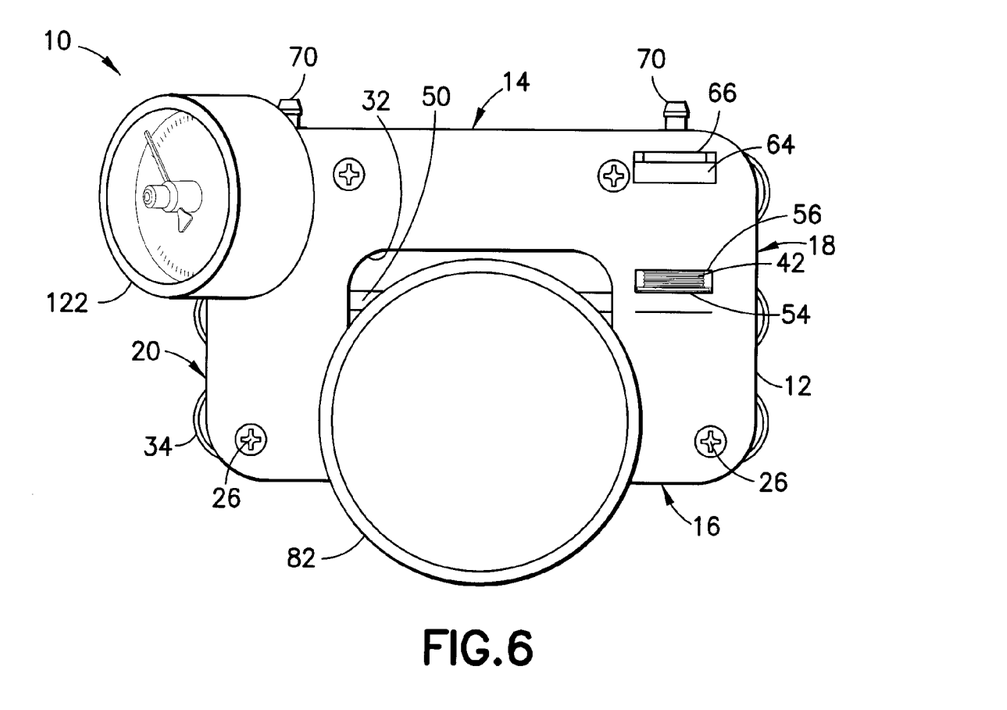
FIG. 6 is a top view of the multi-functional hand strength assessment device shown in FIG. 1.
Figure 7:
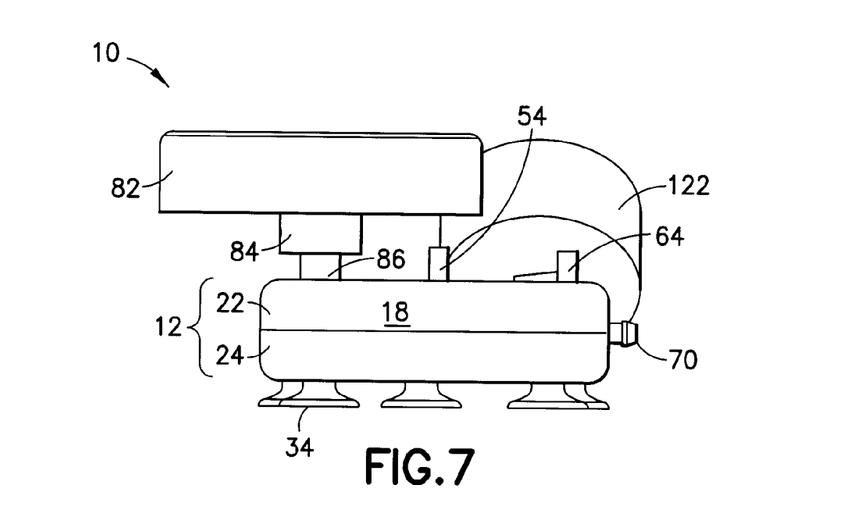
FIG. 7 is a left side view of the multi-functional hand strength assessment device shown in FIG. 1.
Figure 8:
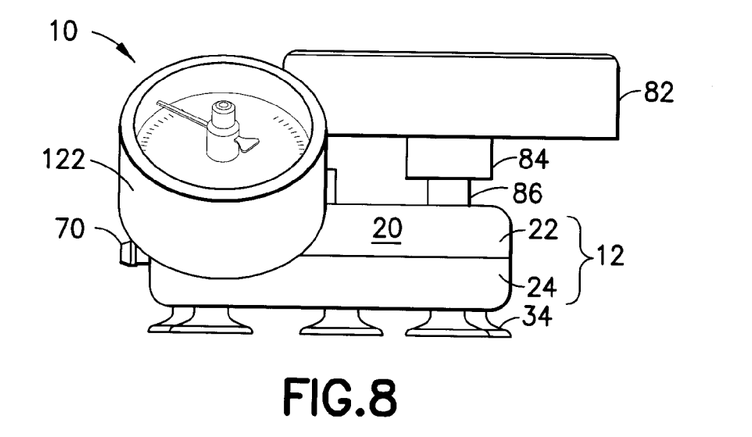
FIG. 8 is a right side view of the multi-functional hand strength assessment device shown in FIG. 1.
Figure 9:
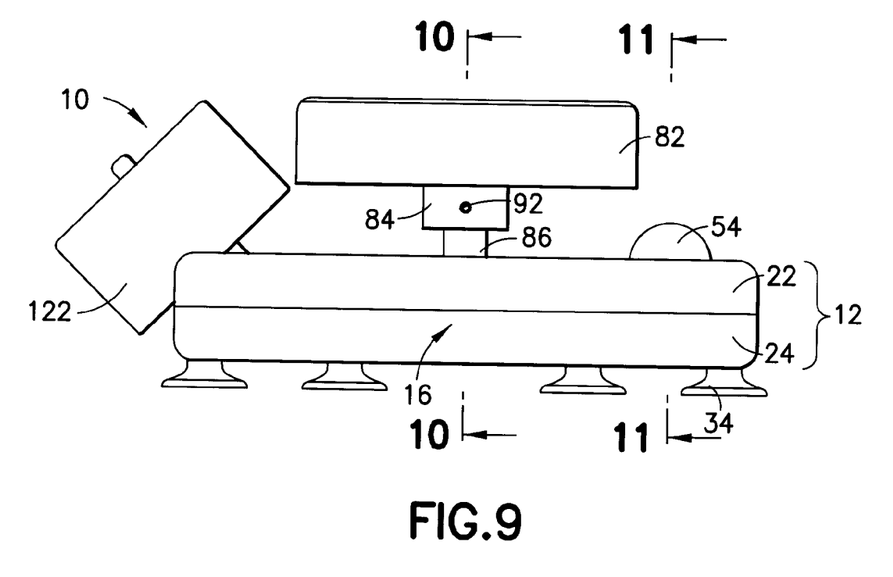
FIG. 9 is a front view of the multi-functional hand strength assessment device shown in FIG. 1.
Figure 10:
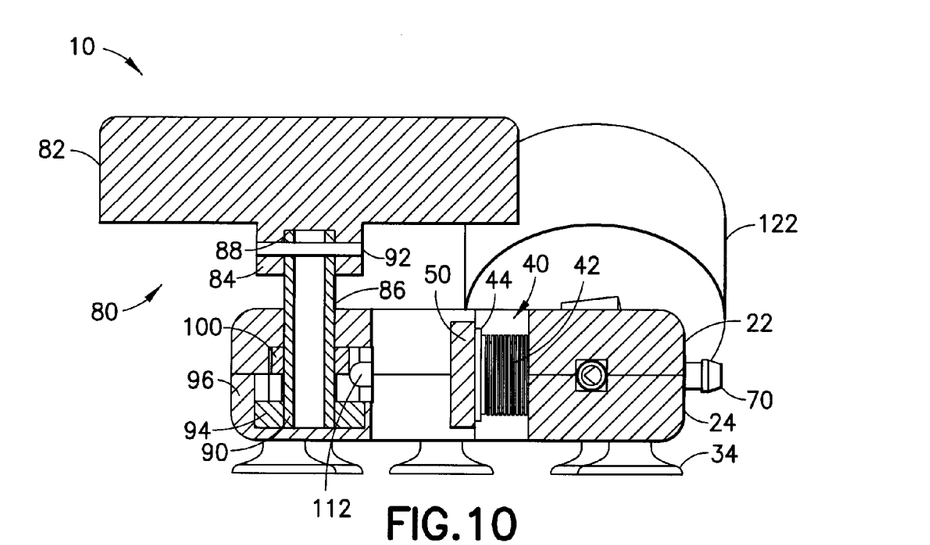
FIG. 10 is a cross-sectional view taken along line 10-10 in FIG. 9.
Figure 11:
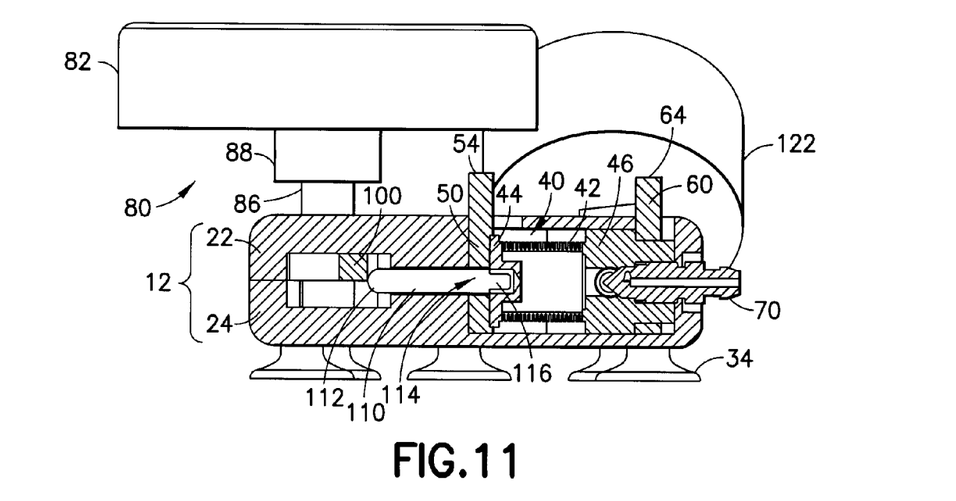
FIG. 11 is a cross-sectional view taken along line 11-11 in FIG. 9.
Figure 12:
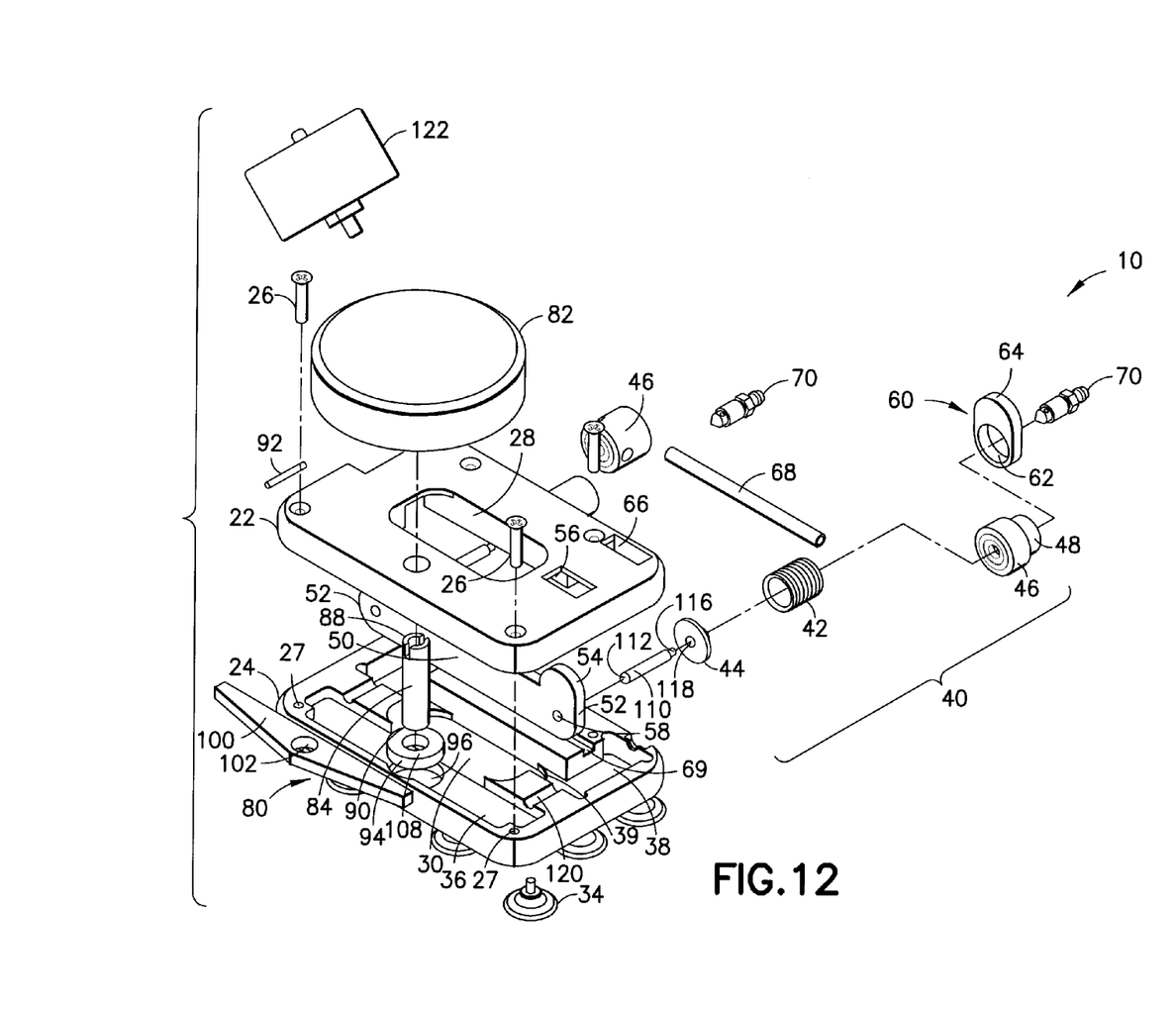
FIG. 12 is an exploded perspective view of the multi-functional hand strength assessment device shown in FIG. 1.
Figure 13:
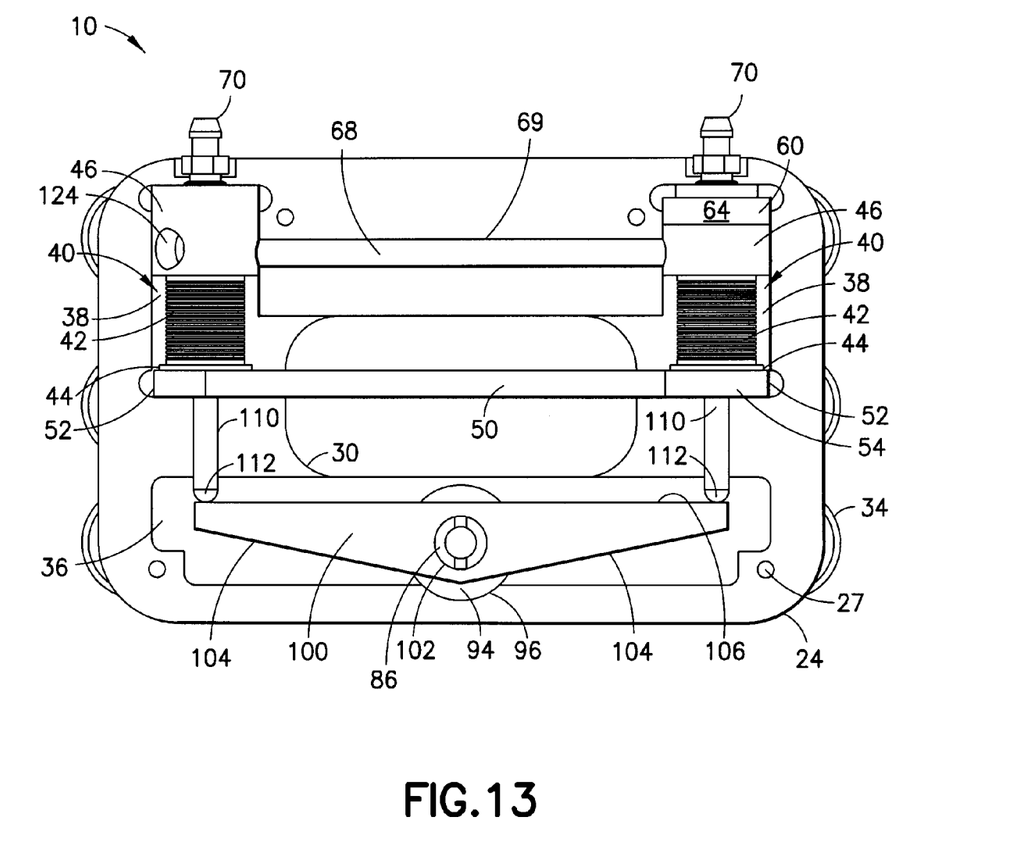
FIG. 13 is a top view showing the interior of the multi-functional hand strength assessment device shown in FIG. 1.

A multi-functional hand strength assessment device 10 is shown in FIGS. 1-13 and permits quantification of three aspects of hand strength, namely, grip hand strength, finger pinch strength, and twisting hand strength in a single mechanical device. The multi-functional hand strength assessment device 10, (hereinafter "device 10") comprises a housing 12 comprising a front longitudinal side 14, a rear longitudinal side 16, and left and right lateral or transverse sides 18, 20. The housing 12 is desirably a multi-piece housing formed by a first or top housing portion 22 that mates to a second or bottom housing portion 24 using conventional mechanical fasteners 26 passing through apertures in the top housing portion 22 and engaging threaded holes 27 in the bottom housing portion 24. Top and bottom housing portions 22, 24 define opposed central openings 28, 30, respectively, which, when the top and bottom housing portions 22, 24 are secured together, define a singular hand access opening 32 sized to receive at least the fingers of the human hand therethrough. A plurality of suction cups 34 may be provided on the bottom surface of bottom housing portion 24 which permit the housing 12 to be secured to a flat surface such as a table top or like surface to allow secure use of the device 10. The suction cups 34 may be replaced by a single large suction cup if desired and other releasable securing arrangements may be provided in place of suction cups 34, such as a mechanical apparatus or a device that releasably connects to a table top or to the end of a table top or like surface to which the device 10 is to be secured. Top and bottom housing portions 22, 24 may be made of any material suitable for a housing of a medical device such as metal, for example, stainless steel or a rigid plastic such as polycarbonate. As illustrated in FIGS. 12-13, bottom housing portion 24 defines a longitudinal recess 36 along a rear longitudinal side of the bottom housing portion 24 and two transverse recesses 38 extending inward from the opposing front longitudinal side of the bottom housing portion 24. The transverse recesses 38 define a dogleg or L-shaped connection 39 with the central opening 30 defined in the bottom housing portion 24. While not illustrated in FIGS. 12-13, it will be clear that top housing potion 22 defines mirroring transverse recesses 38 corresponding to the transverse recesses 38 shown in the bottom housing portion 24 to enclose components of the device 10 in the housing 12.

A bellows device 40 is disposed in each of the transverse recesses 38. Each bellows device 40 comprises a bellows 42, a bellows cap 44 disposed at one end of the bellows 42, and a bellows base 46 disposed at the opposed end of the bellows 42. It will be appreciated that with the two bellows devices 40 disposed in the respective transverse recesses 38 in the bottom housing portion 24, securing of the top housing portion 22 to the bottom housing portion 24 via mechanical fasteners 26 places the two bellows devices 40 in the corresponding transverse recesses 38 in the top housing portion 24. As illustrated, the respective bellows devices 40 are disposed in the transverse recesses 38 with the bellows cap 44 facing the rear longitudinal side 16 of the housing 12 of the device 10 and the bellows base 46 facing the front longitudinal side 14 of the housing 12 of the device 10. Bellows 42 may be made of any suitably resilient material such as rubber and the bellows cap 44 and bellows base 46 may be made of metal, such as steel, stainless steel, or aluminum as examples. One of the bellows base 46, namely, the bellows base 46 associated with the left side bellows device 40 in the orientation of the device 10 defines a recessed end 48.

An elongated grab bar 50 is disposed longitudinally in the bottom housing portion 24 and comprises opposed ends 52 situated in the dogleg or L-shaped connections 39 extending inward from the transverse recesses 38. One of the opposed ends 52 of the grab bar 50 has an arcuate pinch tab 54 that extends upward through a registered opening 56 in the top housing portion 22. An aperture 58 is provided in each end 52 of the grab bar 50. In view of the figures, the pinch tab 54 is located on the left side of the device 10. The grab bar 50 may be made of metal, such as steel, stainless steel, or aluminum as examples.

A pinch bar 60 is associated with the left side bellows device 40 in the orientation of the device 10. The pinch bar 60 defines a central aperture 62 that is disposed about the recessed end 48 of the bellows base 46 of the left side bellows device 40. The pinch bar 60 comprises a pinch tab 64 similar in shape and curvature to the pinch tab 54 on one end 52 of the grab bar 50. The pinch tab 64 on the pinch bar 60 extends upward through a registered opening 66 in the top housing portion 22. The pinch bar 60 may be made of metal, such as steel, stainless steel, or aluminum as examples. A connecting tube 68 fluidly connects the two bellows devices 40 and is disposed in a longitudinal receiving groove 69 defined in the bottom housing portion 24 generally parallel to the grab bar 50. As illustrated in FIG. 12, the connecting tube 68 connects the two bellows devices 40 at the bellows base 46 of the respective bellows devices 40. Additionally, a bleed valve 70 is provided for each of the two bellows devices 40.

A grip assembly 80 is interfaced with the two bellows devices 40 to enable assessment of twisting hand strength of a user of the device 10. The grip assembly 80 comprises a grip 82 comprising an axle 84 that is mechanically interfaced with a rotation shaft 86. The rotation shaft 86 comprises a first or upper end 88 and a second or lower end 90. Grip 82 may be any shape. For example, grip 82 may be wheel-shaped (as shown), pistol grip shape, spherical, polygonal, triangular, or any ergonomic shape that can be easily gripped. The upper end 88 of the rotation shaft 86 is connected with the grip axle 84 via a pin connection 92. A bearing 94 is seated within a bearing recess 96 defined in the longitudinal recess 36 in the bottom housing portion 24. The lower end 90 of the rotation shaft 86 is seated for rotation in the bearing 94 to enable rotation of grip 82. An elongated beam 100 is disposed on the rotation shaft 86 to be pivotal with the rotation shaft 86 as the grip 82 is rotated or turned by the user of the device 10. In particular, the pivotal beam 100 defines a central opening 102 through which the rotation shaft 86 extends to connect the pivotal beam 100 to the grip 82. The pivotal beam 100 is disposed within the elongated longitudinal recess 36 in the bottom housing portion 24. The pivotal beam 100 comprises two tapering longitudinal edges 104 to provide clearance with the longitudinal recess 36 in the bottom housing portion 24 to allow for the pivoting movement of the pivotal beam 100 within the confines of the longitudinal recess 36. A front longitudinal edge 106 of the pivotal beam 100 faces the front longitudinal face or side 14 of the housing 12 of the device 10. Desirably, the engagement of the rotation shaft 86 in the central opening 102 in the pivotal beam 100 is a frictional fit connection such that rotation of the grip 82 and the resulting rotation of the rotation shaft 86 imparts right or left (e.g., clockwise or counterclockwise) pivotal movement to the pivotal beam 100 depending on whether the grip 82 is turned clockwise or counterclockwise. The pivotal beam 100 is assembled with the rotation shaft 86 such that a bottom surface of the pivotal beam 100 sits on a top face 108 of the bearing 94 to enable substantially free pivotal movement of the pivotal beam 100 in the longitudinal recess 36. Desirably, the top face 108 of the bearing 94 is slightly elevated above the surface of the longitudinal recess 36. Such a raised or elevated position of the top face 108 of the bearing 94 raises the pivotal beam 100 above immediate surface contact with the longitudinal recess 36 and frees the pivotal beam 100 from frictional contact with the bottom housing portion 24 in the longitudinal recess 36 which could hinder the pivotal movement of the pivotal beam 100.

The grip assembly 80 is operationally interfaced with the two bellows devices 40 via a pair of push pegs 110 which mechanically interface with the bellows devices 40, respectively. In particular, the push pegs 110 comprise a first, rounded end 112 adapted to contact one of the front longitudinal edges 106 of the pivotal beam 100 and a second end 114 with a pin tip 116 which is received in a mating opening 118 defined in the bellows cap 44 of the respective bellows devices 40. The respective push pegs 110 extend through respective channels 120 extending from the longitudinal recess 36 in the bottom housing portion 24 and through the apertures 58 in the grab bar 50 to engage the respective bellow cap 44. Desirably, the connection between the pin tip 116 at the second end 114 of the respective push pegs 110 with the mating opening 118 in the bellows cap 44 of the respective bellows devices 40 is a friction fit connection of sufficient strength to prevent separation of the push pegs 110 from the two bellows caps 44. In view of the interconnection between the push pegs 110 and the bellows caps 44, right or left (e.g., clockwise or counterclockwise) pivotal movement of the pivotal beam 100 results in contact with the rounded end 112 of one of the push pegs 110 and this push peg 110 thereafter acts upon the associated bellows cap 44.

Desirably, the components of the grip assembly 80 are formed of metal, such as steel, stainless steel, or aluminum, with the exception of the bearing 94 which is desirably made of a material that permits free rotational movement of the rotation shaft 86 in the bearing 94. A pressure gauge 122 is associated with the right side bellows device 40 via a side port 124 provided in the bellows base 46 of the bellows device 40. Such a pressure gauge 122 may be a conventional mechanical pressure gauge or an equivalent electronic air pressure gauge as desired. The pressure gauge 122 is fluidly interfaced to the right side bellows device 40 via the side port 124 and the fluid interconnection between the two bellows devices 40 provided by the connecting tubing 68 between the bellows devices 40 and this fluid interconnection allows the compression of either bellows device 40 to be registered as an increase in pressure on the pressure gauge 122. A side opening 126 may be provided in the top housing portion 22 to allow connection of the pressure gauge 122 with the right side bellows device 40.

With continued reference to FIGS. 1-13, operation of the device 10 to assess grip hand strength, finger pinch strength, and twisting or torque hand strength will now be discussed. In the assessment of grip hand strength, the user of the device 10 insert his or her fingers though the central hand access opening 32 in the housing 12 to grasp the grab bar 50 while the user's palm and thumb contact the front longitudinal side 14 of the housing 12. Pressure applied to the grab bar 50 by gripping the housing 12 and the grab bar 50 substantially simultaneously compresses the bellows 42 of the two bellows devices 40 via the contact engagement between the opposed ends 52 of the grab bar 50 with the respective bellows caps 44 of the two bellows devices 40. The compression of the bellows 42 substantially simultaneously registers a pressure increase on the pressure gauge 122 via the fluid connectivity between the bellows devices 40 and the pressure gauge 122.

In the assessment of finger pinch strength, the user of the device 10 places the finger to be tested on the pinch tab 54 projecting upward from the left end 52 of the grab bar 50 and his or her thumb or another digit on the pinch tab 64 projecting upward from the pinch bar 60. The respective pinch tabs 54, 64 may be contacted as desired and the foregoing illustrative example should not read as limiting. The user then substantially simultaneously squeezes the pinch bar 60 and the elevated pinch tab 54 on the grab bar 50 and compresses one of the two bellows devices 40, namely, the left side bellows device 40 in the orientation of the device 10. The compression of this bellows device 40 registers a pressure increase on the pressure gauge 122 via the fluid connectivity between the bellows devices 40 and the pressure gauge 122.

In the assessment of twisting or torque hand strength, the user places the hand to be tested on the grip 82 and turns the grip 82 either clockwise or counterclockwise. Turning of the grip 82 results in rotation of the rotation shaft 86 which imparts right or left pivotal (e.g., clockwise or counterclockwise) movement to the pivotal beam 100 depending on whether the grip 82 is turned clockwise or counterclockwise. The pivoting movement of the pivotal beam 100 causes the beam to push on one of the two push pegs 110, thereby pushing on the associated bellows cap 44 and compressing the associated bellows 42. It will be apparent that counterclockwise twisting compresses one push peg 110 and clockwise twisting compresses the other push peg 110. Additionally, the compression of the actuated bellows device 40 registers a pressure increase on the pressure gauge 122 via the fluid connectivity between the two bellows devices 40 and the pressure gauge 122. In each of the foregoing test cases, force applied to bellows caps 44 causes pressure in the associated bellows 42 and the pressure is sensed by the pressure gauge 122 which displays the pressure in analog form or in electronic form.

Figure 14:
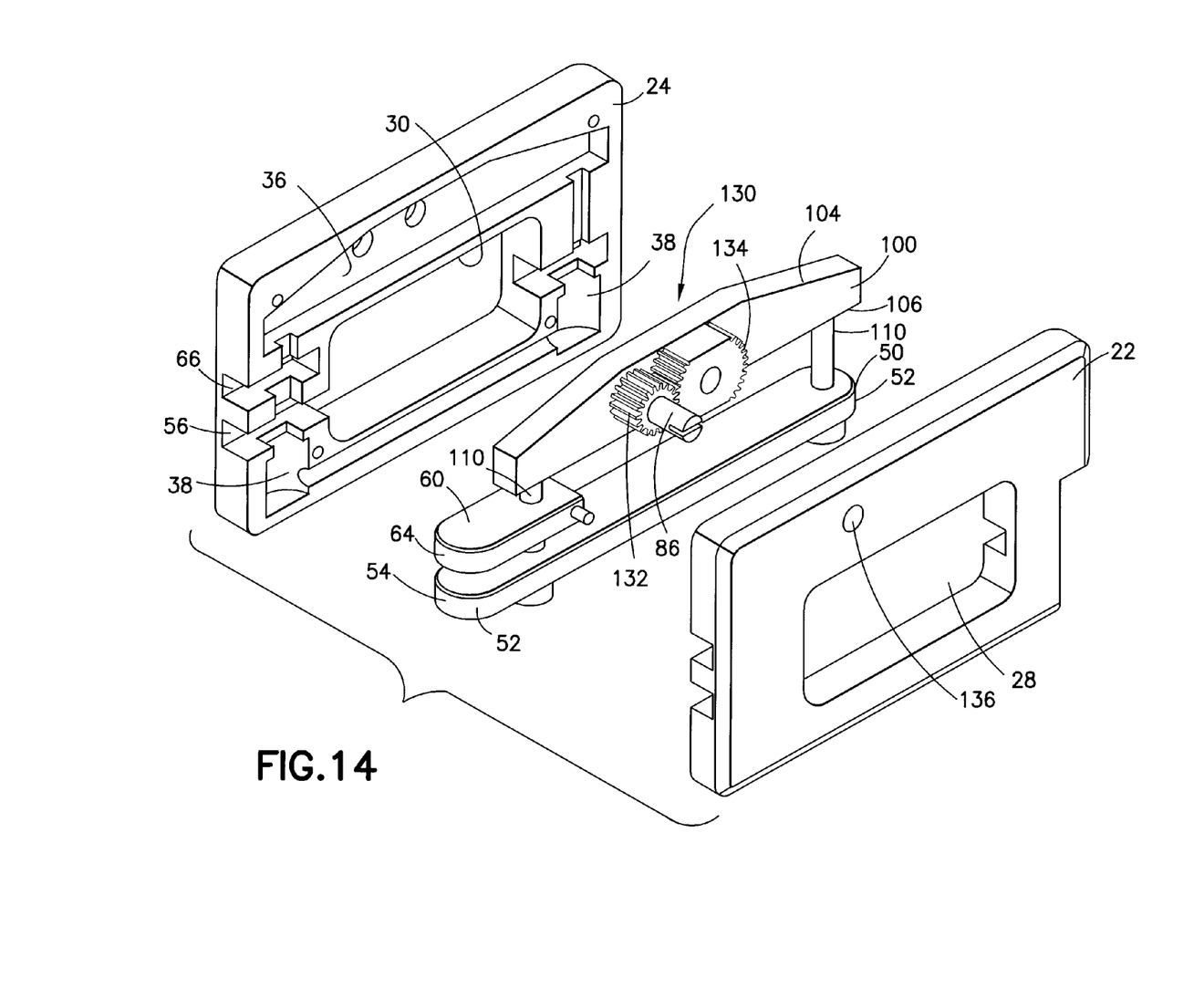
FIG. 14 is an exploded perspective view of the housing and a pivotal beam-grab bar mechanism according to another embodiment.

FIG. 14 shows another embodiment of the housing and the pivotal beam-grab bar mechanism. Compared to the previously shown embodiments, this embodiment differs by positioning pinch tabs 54 and 64 and related openings 56 and 66 to the side of the housing instead of at the top of the housing. The pinch tabs 54 and 64 now function as a pivoting lever, instead of a sliding lever. Also, a gear mechanism 130 is included to actuate the bellows 40. The inside of the housing 12 constrains the bellows from expansion when only one side is pressurized.

The push pegs 110 are the means by which load is applied to the bellows 40, but push pegs 110 have steps with different diameters, widening at the base 112. The step closest to the bellows 40 now supports the grab bar 50. While the peg 110 on the right has one step, the peg 110 on the left in FIG. 14 has two steps. The step closest to the bellows 40 again supports the grab bar 50. The step further away from the bellows 40 now supports the pinch bar 60.

The pinch bar 60 is a lever and functions by pushing on the step of the push peg 110. The pinch bar 60 has a hole larger than the step and the push peg 110 passes through this hole. The hole, however, is smaller than the step so that the pinch bar 60 has a small amount of rotation which allows it contact the push peg 110 when a pinch test is conducted.

Gear mechanism 130 includes rotation gear 132 which is mechanically coupled to rotation shaft 86 and pivot shaft 134 which is coupled to pivotal beam 100. Pivot shaft 134 is fixed to pivotal beam 100 and both elements pivot about the center of pivot shaft 134. Pivot shaft 134 has a plurality of cogs disposed thereon for mechanically interfacing with rotation gear 132. Rotation gear 132 and rotation shaft 86 are held in place by mechanically interfacing with aperture 136 of top housing portion 22. Shaft 86 protrudes through aperture 136 when the device is assembled. Aperture 136 may have a bearing and/or a bushing for interfacing with rotation shaft 86. The gear mechanism 130 is used to drive the pivot beam 100 and is included so that the tests described previously each use the pressure range available on the pressure gauge 122. The diameter of the gears and/or shafts can be adjusted to change the grip force needed to drive pivot beam 100 and therefore can be adjusted to properly use the pressure range of the pressure gauge 122. Without the gear mechanism 130, the twist readings may result in lower pressures than the actual grip pressures or forces. Similarly, the location of the pivot for the pinch tab 64 lets the pressures in the pinch test approximate those in the grip and twist tests.

While embodiments of a multi-functional hand strength assessment device and methods of operation thereof were provided in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A multi-functional hand strength assessment device, comprising:
   a housing;
   at least one bellows device supported by the housing;
   a grip bar interfaced with the bellows device for compression thereof, the grip bar supported by the housing and accessible by a user to grasp the grip bar for selective assessment of grip hand strength and finger pinch strength of the user; and
   a grip interfaced with the bellows device for compression thereof for assessment of twisting hand strength of the user.

2. The multi-functional hand strength assessment device as claimed in claim 1, further comprising a pinch bar supported by the housing opposite the grip bar and wherein movement of one of the grip bar and the pinch bar towards the other compresses the bellows device for assessment of finger pinch strength of the user's fingers.

3. The multi-functional hand strength assessment device as claimed in claim 2, wherein the grip bar comprises an upstanding pinch tab for contact by the user's fingers.

4. The multi-functional hand strength assessment device as claimed in claim 1, further comprising a pressure gauge in fluid connection with the bellows device.

5. The multi-functional hand strength assessment device as claimed in claim 4, wherein the pressure gauge is one of a mechanical pressure gauge and an electronic pressure gauge.

6. The multi-functional hand strength assessment device as claimed in claim 1, further comprising at least one suction cup provided on the bottom of the housing for securing the housing to a support surface.

7. The multi-functional hand strength assessment device as claimed in claim 1, wherein the grip bar is in contact engagement with the bellows device such that linear movement of the grip bar compresses the bellows device.

8. The multi-functional hand strength assessment device as claimed in claim 1, wherein the grip is interfaced with the bellows device via a pivotal beam connected to the grip such that rotational movement of the grip pivots the beam and compresses the bellows device.

9. A multi-functional hand strength assessment device, comprising:
   a housing;
   at least one bellows device supported by the housing;
   a grip bar interfaced with the bellows device for compression thereof, the grip bar supported by the housing and accessible by a user to grasp the grip bar for assessment of grip hand strength; and
   a pinch bar supported by the housing opposite the grip bar.

10. The multi-functional hand strength assessment device as claimed in claim 9, wherein movement of one of the grip bar and the pinch bar towards the other compresses the bellows device for assessment of finger pinch strength of the user's fingers.

11. The multi-functional hand strength assessment device as claimed in claim 9, wherein the grip bar comprises an upstanding pinch tab for contact by the user's fingers.

12. The multi-functional hand strength assessment device as claimed in claim 9, further comprising a pressure gauge in fluid connection with the bellows device.

13. The multi-functional hand strength assessment device as claimed in claim 12, wherein the pressure gauge is one of a mechanical pressure gauge and an electronic pressure gauge.

14. The multi-functional hand strength assessment device as claimed in claim 9, further comprising at least one suction cup provided on the bottom of the housing for securing the housing to a support surface.

15. A multi-functional hand strength assessment device, comprising:
   a housing;
   at least one bellows device supported by the housing;

a grip bar interfaced with the bellows device for compression thereof, the grip bar supported by the housing and accessible by a user to grasp the grip bar for assessment of grip hand strength; and a grip interfaced with the bellows device for compression thereof for assessment of twisting hand strength of the user.

16. The multi-functional hand strength assessment device as claimed in claim 15, further comprising a pressure gauge in fluid connection with the bellows device.

17. The multi-functional hand strength assessment device as claimed in claim 16, wherein the pressure gauge is one of a mechanical pressure gauge and an electronic pressure gauge.

18. The multi-functional hand strength assessment device as claimed in claim 15, further comprising at least one suction cup provided on the bottom of the housing for securing the housing to a support surface.

19. The multi-functional hand strength assessment device as claimed in claim 15, wherein the grip bar is in contact engagement with the bellows device such that linear movement of the grip bar compresses the bellows device.

20. The multi-functional hand strength assessment device as claimed in claim 15, wherein the grip is interfaced with the bellows device via a pivotal beam connected to the grip such that rotational movement of the grip pivots the beam and compresses the bellows device.

21. A method of operating a multi-functional hand strength assessment device, comprising the steps of:
providing the multi-functional hand strength assessment device, comprising:
a housing;
at least one bellows device supported by the housing;
a grip bar interfaced with the bellows device for compression thereof; and
a grip interfaced with the bellows device for compression thereof;
grasping one of the grip bar and grip; and
actuating the selected grip bar or grip to compress the bellows device.

22. The method as claimed in claim 21, further comprising at least one suction cup provided on the bottom of the housing, and the method further comprising securing the housing to a support surface using the at least one suction cup.

23. The method as claimed in claim 21, wherein the grip bar is in contact engagement with the bellows device, and the method further comprising effecting linear movement of the grip bar to compress the bellows device.

24. The method as claimed in claim 21, wherein the grip is interfaced with the bellows device via a pivotal beam connected to the grip, and the method further comprising effecting rotational movement of the grip to pivot the beam and compress the bellows device.

25. The method as claimed in claim 21, further comprising a pinch bar supported by the housing opposite the grip bar, and the method further comprising moving one of the grip bar and the pinch bar towards the other to compress the bellows device.

26. The method as claimed in claim 21, further comprising a pressure gauge in fluid connection with the bellows device, and the method further comprising assessing one of grip hand strength, finger pinch strength, and twisting hand strength of the user using the pressure gauge upon compression of the bellows device.

* * * * *